United States Patent
Falcovitz-Gerassi et al.

(10) Patent No.: US 7,258,990 B2
(45) Date of Patent: Aug. 21, 2007

(54) ALLEVIATION OF NON-SPECIFIC BINDING IN MICROARRAY ASSAYS

(75) Inventors: Yehudit Falcovitz-Gerassi, San Diego, CA (US); Pavel Tsinberg, Carlsbad, CA (US)

(73) Assignee: Biocept, Inc., San Diego, CA (US)

(*) Notice: Subject to any disclaimer, the term of this patent is extended or adjusted under 35 U.S.C. 154(b) by 208 days.

(21) Appl. No.: 10/922,387

(22) Filed: Aug. 19, 2004

(65) Prior Publication Data

US 2006/0040407 A1 Feb. 23, 2006

(51) Int. Cl.
*G01N 33/53* (2006.01)

(52) U.S. Cl. .......... 435/7.1; 435/283.1; 435/287.1; 435/287.2; 435/288.4; 435/288.7; 422/50; 422/61; 422/55; 422/68.1; 422/82.08

(58) Field of Classification Search .......... 435/7.1, 435/283.1, 287.1, 287.2, 288.4, 288.7; 422/50, 422/61, 55, 68.1, 82.08; 436/518, 528, 535
See application file for complete search history.

(56) References Cited

U.S. PATENT DOCUMENTS

| | | | | |
|---|---|---|---|---|
| 4,732,852 | A * | 3/1988 | Cohen et al. | 435/68.1 |
| 4,829,009 | A | 5/1989 | Graves | 436/518 |
| 5,017,559 | A | 5/1991 | Dosako et al. | 514/21 |
| 5,149,626 | A * | 9/1992 | Fleming | 435/7.9 |
| 5,210,020 | A | 5/1993 | Kondo et al. | 435/7.94 |
| 5,248,595 | A | 9/1993 | Boyer et al. | 435/7.32 |
| 5,656,504 | A | 8/1997 | Johansson et al. | 436/518 |
| 5,686,315 | A * | 11/1997 | Pronovost et al. | 436/510 |
| 6,174,683 | B1 | 1/2001 | Hahn et al. | 435/6 |
| 6,942,970 | B2 * | 9/2005 | Isola et al. | 435/6 |
| 6,994,971 | B1 * | 2/2006 | Straume et al. | 435/6 |
| 2001/0049108 | A1 | 12/2001 | McGall et al. | |
| 2003/0044823 | A1 | 3/2003 | Wolf et al. | 435/6 |
| 2003/0092090 | A1 * | 5/2003 | Hajizadeh et al. | 435/7.92 |
| 2003/0134294 | A1 * | 7/2003 | Sandford et al. | 435/6 |
| 2004/0153256 | A1 * | 8/2004 | Woods | 702/27 |

FOREIGN PATENT DOCUMENTS

WO WO 02/059372 8/2002

OTHER PUBLICATIONS

Database Medline 'Online! US National Library of Medicine (NLM), Bethesda, MD, US; Aug. 1991, Puvion-Dutilleulf et al: "Ultrastructural localization of defined sequences of viral RNA and DNA by in situ hybridization of biotinylated DNA probes on sections of herpes simplex virus type 1 infected cells"; XP002362782 Database accession No. NLM1656002 abstract & Journal of Electron Microscopy Technique; Aug. 1991, vol. 18, No. 4, Aug. 1991, pp. 336-353, ISSN: 0741-0581.
Hayashi Toshio et al: "Protease immobilization onto polyacrolein microspheres", Biotechnol Bioeng, Biotechnology and Bioengineering, Mar. 5, 1990, vol. 35, No. 5, Mar. 5, 1990, pp. 518-524, XP002362780 the whole document.

* cited by examiner

*Primary Examiner*—Long V. Le
*Assistant Examiner*—Melanie J. Yu
(74) *Attorney, Agent, or Firm*—Fitch, Even, Tabin & Flannery

(57) ABSTRACT

A post-incubation treatment is employed to effectively remove targets, such as proteins/protein complexes, or other label-bearing moieties that may non-specifically bind to a microarray substrate during a binding assay. Following incubation, a one-step wash is carried out with a liquid containing digester, e.g., a digestive enzyme (protease) or lysosome, which is effective to remove non-specifically bound targets or at least labeled portions of such targets from the substrate. Proteases are bound to or coated onto large molecules or onto solid particles of such a size such that they are prohibited from entering the porous surfaces of 3-D hydrogel microspots and are unable to reach and digest labeled target-probe complexes that are disposed within such porous hydrogel microspots. Digested segments of such protein which contain labels (or of essentially the entire protein) are carried away in the wash liquid and thus are not present to create background noise during imaging.

24 Claims, No Drawings

US 7,258,990 B2

ALLEVIATION OF NON-SPECIFIC BINDING IN MICROARRAY ASSAYS

This application relates to methods of assaying for targets in an unknown sample, and more particularly to methods of assaying for targets, e.g., proteins or cell lysates, using a microarray wherein steps are taken to minimize background noise that would otherwise result from non-specific target or other binding to the microarray substrate and would interfere with measuring signals from such microarrays.

BACKGROUND OF THE INVENTION

Background binding of proteins, carbohydrates, cell lysates and the like to glass or other substrates employed in microarrays which include microspots containing protein capture agents or the like has posed a problem for a number of years. Non-specific binding of proteins to a microarray substrate increases the background noise when the microarray is imaged or the signals generated on the microspots are otherwise read; this makes it difficult to detect and distinguish signals being obtained from labels which should be specifically bound to particular spots, particularly in instances where the signal is relatively weak, because such background noise interferes and prevents obtaining precise readings.

To date two of the more common methods being used to attempt to alleviate or mitigate this problem involve manners of blocking the regions of the surface of the substrate surrounding each of the plurality of microspots. Such blocking has been done by chemically coating the surface of the substrate, e.g., by carrying out chemical reactions with the amino groups with which the glass surface has often been derivatized, as for example using succinic anhydride. A second method has employed the attachment of small molecules to the glass surface, for example, BSA, tRNA, skim milk solids, casein and the like. Various of these blocking methods are described in U.S. Patent Publication No. 2003/004823 which itself proposes the use of a "spreading enhancer solution" that would presumably be effective in assays employing nucleic acid probes. U.S. Pat. No. 5,248,595 is concerned with assays which employ antibodies, and it suggests removing uncomplexed protein materials using an aqueous wash, buffered to pH 9 or above and containing a specific anionic surfactant. U.S. Pat. No. 5,656,504 is concerned with assays employing antibodies, and it discloses coating glass supports with a layer of carboxylated dextran to prevent the undesired binding of proteins. U.S. Pat. No. 5,017,559 suggests blocking non-specific absorption of antibodies or the like onto a substrate by the use of milk protein plus a specific percentage of an organic acid.

Although various of these proposed solutions to the problem have shown some success, none of them has been widely accepted as the total solution to this problem. Accordingly the search has gone on for better solutions for combating background noise in reading microarrays, and particularly for those which use three-dimensional (3-D) hydrogel microspots.

SUMMARY OF THE INVENTION

It has been found that a particular post-incubation treatment can be employed to effectively remove targets, such as proteins/protein complexes, or other label-bearing moieties that may non-specifically bind to a microarray substrate during a binding assay. Following incubation, a one-step wash is carried out with a liquid containing digester, e.g., a digestive enzyme (protease) or lysosome, which is effective to remove such labels, such as by removing fluorescent-labeled portions of targets and/or by removing the targets themselves, from the substrate to which such targets may have become non-specifically bound. These proteases are bound to or coated onto molecules or solid particles of such a size such that they will be prohibited from entering the porous surfaces of the 3-D hydrogel microspots; thus, they will be unable to reach and digest the labeled target-probe complexes that are disposed within the porous hydrogel microspots. Single or multiple proteases or other digesters can be employed depending upon the demands of a particular assay. Once a particular segment of a protein containing the label (or essentially the entire protein) has been cleaved, it will be carried away in this wash liquid. In instances, for example, where the assay is a sandwich assay employing multiple antibodies, it may be desirable either to employ multiple proteases or to carry out multiple washes using different proteases.

In one particular aspect, the invention provides a method for the determination of the presence of one or more targets in a sample being analyzed, which method comprises: providing a substrate having an upper surface, attaching a plurality of 3-dimensional porous microspots of hydrogel to said surface, providing different capture agents within the pores of various of said plurality of microspots to create a microarray on said surface, contacting said microarray with a solution containing targets of a size that allows binding with said capture agents within said porous hydrogel microspots, washing said microarray following said contacting using a liquid containing a digester which removes non-specifically bound targets or at least labeled portions thereof from said surface without affecting targets specifically bound to capture agents within said porous hydrogel microspots, associating labels with said targets either before or after said washing if said targets do not comprise labels at the time of said binding, and measuring said washed microarray to detect signals from labeled targets bound within particular microspots.

In another particular aspect, the invention provides a method for the determination of the presence of one or more targets in a sample being analyzed, which method comprises: providing a solid substrate having an upper surface, attaching a plurality of 3-dimensional porous microspots of isocyanate-functional hydrogel to said surface, immobilizing binding entities within said porous hydrogel microspots, providing different proteinaceous capture agents within the pores of various of said plurality of microspots to create a microarray, by diffusing such capture agents in an aqueous solution into said porous hydrogel microspots so as to by attach to said binding entities, contacting said microarray with an aqueous solution containing targets of a size that allows binding with said capture agents within said porous hydrogel microspots, washing said microarray following said contacting using a liquid containing a digester which removes non-specifically bound targets or at least any labeled portions thereof from said surface without affecting targets specifically bound to capture agents within said porous hydrogel microspots, and measuring said washed microarray to detect signals from labeled targets bound within particular microspots.

DETAILED DESCRIPTION OF THE PREFERRED EMBODIMENTS

Immunological assays in medical diagnostic fields have, in recent years, utilized solid phase substrates e.g. plates, such as glass microscope slides and those made of silicon, as well as nitrocellulose membranes and the like, to support probes or capture agents specific to certain molecules in order to determine the presence or absence of a particular ligand in an unknown sample. Accordingly, substrates used to prepare microarrays for assaying have included supporting films or microporous membranes, solid flat plates and plates, which may be porous or impermeable, that have a plurality of microwells. Glass slides, such as standard microscope slides, are commonly employed as substrates for such microarrays, and such glass surfaces are often treated with an aminosilane, an aldehyde, polylysine or the like to provide a surface of a reactivity receptive to binding probes or materials to which probes will be attached. Aminosilane treatment of glass slides is often used for this purpose to provide such substrates.

The present invention is concerned with the employment of microarrays which have a plurality of 3D microspots; microarrays are sometimes referred to as biochips. Examples of such biochips are described in U.S. Pat. No. 6,174,683 and in published international application WO 02/059372, entitled "Three Dimensional Format Biochips."

In such a three-dimensional array, the probes are not connected to the solid surface of a well in a plate, or to a glass slide or some other flat plate, or to a microporous membrane or film; instead they are presented in a three-dimensional array by attachment within microspots of porous, polymerized hydrogel. This arrangement isolates the probes from the solid substrate and presents an expanded surface area for presentation of the probes and for the ultimate capture of labeled molecules or the like. A plurality of such 3D microspots are normally provided on each glass slide or in each well of a microwell plate or the like.

The biochip substrate may be made from a variety of materials, and it will usually have a format which is conducive both to automated handling during a binding assay and to later detection of target molecules which bind to the individual microspots. Although solid flat plates, e.g. glass slides, are suitable and are preferably employed, plates that have depressions or wells formed therein to hold individual microspots may also be used. Some microporous membranes, such as nitrocellulose or nylon membranes, may be employed so long as there would be access for the digester to the surfaces where non-specific binding may occur. An optically transparent substrate, such as glass or clear polystyrene, will allow for transmission light detection through the microspots and is convenient for detection modalities using fluorescence or optical absorption. Due to the high binding capacity of three-dimensional hydrogel microspots, reflective optical methods are also possible and allow the use of opaque substrates. The use of rigid substrates allows for precision of alignment during the detection phase of analysis using a biochip, but such may not be necessary if proper alignment is incorporated into the microspots to facilitate detection. For example, a flexible format, such as a tape, microporous membrane or filament, could be precisely detected in a scanning fashion similar to the use of magnetic tape. While optical methods and suitable substrates are preferred due to their simplicity, other biochemical detection methods might alternatively be used, e.g. the detection of ofiradioactive labels. Generally, any number of microspots can be provided on a biochip, e.g. from 1 to 10,000. To assist automated handling, often multiples of 96 may be used; for example, 384 microspots may be provided in an array on a 3 in (7.6 cm)×5 in (12.7 cm) plate.

Hydrogels are a class of polymers that can provide a gel matrix that has the following desirable attributes: adequate pore size and high water content to permit diffusion of molecules in and out of the matrix, the ability to bind to the surface of glass other impermeable or microporous surface, optical transparency in a fully polymerized state to minimize optical interference with fluorescent tags, good structural integrity when fully polymerized, and adequate shelf life for normal research and clinical use. Hydrogels are hydrophilic network polymers which are glassy in the dehydrated state and which swell in the presence of water to form an elastic gel. Isocyanate-functional hydrogels possess a number of characteristics that can be used to advantage for the immobilization of capture agents, such as nucleic acid hybridization probes, proteins, carbohydrates, cells, etc. By isocyanate-functional hydrogels are meant organic polymers that are capped with isocyanate groups that will function to carry out a desired further polymerization and also covalently bind proteins or the like, or intermediates that in turn bind proteins. For example, polyurethane polymers, which are well known in the art and which can be formed by reactions between diisocyanates and polyether or polyester polyols, can provide suitable hydrogels for this purpose.

Prepolymers are generally used as starting material to form biochips using such isocyanate-functional hydrogels, and such prepolymers may be formulated to provide hydrated polyurethane, polyurea-urethane and/or polyurea polymeric gels. Hydrogel polymers are typically formed by polymerizing a hydrophilic monomer in an aqueous solution under conditions such that a lightly cross-linked prepolymer is initially formed having a three-dimensional polymeric network which gels in concentrated form. Polyurethane hydrogels can be formed by the polymerization of isocyanate-end-capped prepolymers by the creation of urea and urethane linkages.

Suitable isocyanate-functional prepolymers are often prepared from relatively high molecular weight polyoxyalkylene diols or polyols which are reacted with bi-functional or multi-functional isocyanate compounds. Preferred prepolymers for use in making biochips are made from polyoxyalkylene diols or polyols that may comprise homopolymers of ethylene oxide units or block or random copolymers containing mixtures of ethylene oxide units and propylene oxide or butylene oxide units. In the case of block or random copolymers, at least 75% of the units should preferably be ethylene oxide units. Homopolymers of polypropylene oxide may alternatively be employed. A polyoxyalkylene diol or polyol from 5,000 to 30,000 molecular weight is preferably used, and suitable prepolymers are prepared by reacting selected polyoxyalkylene diols or polyols with polyisocyanate, at an isocyanate-to-hydroxyl ratio of about 1.2 to about 2.2 so that essentially all of the hydroxyl groups are capped with polyisocyanate. Such an isocyanate-functional prepolymer preferably contains active isocyanates in an amount of about 0.2 meq/g to about 0.8 meq/g. The prepolymer should not polymerize too rapidly in forming microspots, and in this respect, high molecular weight prepolymers containing a relatively low isocyanate content are generally preferred.

Such high molecular weight prepolymers are often prepared by either of two general methods: (1) a polyol (triol or higher) having a molecular weight of at least 2000 is reacted with a polyisocyanate, such as isophorone diisocyanate, or (2) a diol having a molecular weight of at least 2000 is reacted with a polyisocyanate and a cross-linking agent, such as glycerol, trimethylolpropane, trimethylolethane, triethanolamine or an organic triamine.

Aromatic, aliphatic or cycloaliphatic polyisocyanates may be used. High molecular weight aliphatic isocyanate-capped prepolymers typically gel to a hydrated polymer state in about 20 to 90 minutes, whereas prepolymers capped with aromatic polyisocyanates gel much more rapidly. Examples of suitable bi- and multi-functional isocyanates are as follows: toluene-2,4-diisocyanate, toluene-2,6-diisocyanate, isophorone diisocyanate, ethylene diisocyanate, ethylidene diisocyanate, propylene-1,2-diisocyanate, cyclobexylene-1,2-diisocyanate, cyclohexylene-1,4-diisocyanate,-phenylene diisocyanate, 3,3"-diphenyl-4,4"-biphenylene diisocyanate, 1,6-hexamethylene diisocyanate, 1,4-tetramethylene diisocyanate, 1,10-decamethylene diisocyanate, cumene-2,4-diisocyanate, 1,5-naphthalene diisocyanate, methylene dicyclohexyl diisocyanate, 1,4-cyclohexylene diisocyanate, p-tetramethyl xylylene diisocyanate, p-phenylene diisocyanate, 4-methoxy-1,3-phenylene diisocyanate, 4-chloro-1,3-phenylene diisocyanate, 4-bromo-1,3-phenylene diisocyanate, 4-ethoxyl-1,3-phenylene diisocyanate, 2,4-dimethyl-1,3-phenylene diisocyanate, 2,4-dimethyl-1,3-phenylene diisocyanate, 5,6-dimethyl-1,3-phenylene diisocyanate, 1,4-diisocyanatodiphenylether, 4,4'-diisocyanatodi-phenylether, benzidine diisocyanate, 4,6-dimethyl-1,3-phenylene diisocyanate, 9,10-anthracene diisocyanate, 4,4'-diisocyanatodi-benzyl, 3,3'-dimethyl-4,4'-diisocyanatodiphenylmethane, 1,6-dimethyl-4,4'-diisocyanatodiphenyl, 2,4-diisocyanatostibene, 3,3'-dimethoxy-4,4'-diisocyanatodiphenyl, 1,4-antracenediisocyanate, 2,5-fluoronediisocyanate, 1,8-naphthalene diisocyanate, 2,6-diisocyanatobenzluran, 2,4,6-toluene triisocyanate, p,p',p"-triphenylmethane triisocyanate, trifunctional trimer (isocyanurate) of isophorone diisocyanate, trifunctional biuret of hexamethylene diisocyanate, trifunctional trimer (isocyanurate) of hexamethylene diisocyanate, polymeric 4,4'-diphenylmethane diisocyanate, xylylene diisocyanate and m-tetramethyl xylylene diisocyanate.

Capping of a selected diol or polyol with a polyisocyanate to form a prepolymer may be effected using stoichiometric amounts of reactants. The isocyanate-to-hydroxyl group ratio may vary as known in this art but is, preferably, about 1.2 to about 2.2. The capping reaction is carried out using suitable conditions, such as at about 60° to 100° C., under dry nitrogen, for about 2 hours to about 14 days, and preferably in the absence of a catalyst. The reaction terminates when the isocyanate concentration approximates theoretical values.

Preferred prepolymers include polyethylene glycol that is end-capped with toluene diisocyanate; a copolymer of ethylene oxide and propylene oxide (optionally with trimethylolpropane) and toluene diisocyanate; toluene diisocyanate-polyethylene glycol-trimethylopropane, methylene diisocyanate-methylene homopolymer; polymeric methylene diisocyanate-polyethylene glycol; polymer of ethylene oxide-propylene oxide-trimethylolpropane and isophorone diisocyanate; and polyethylene glycol trilactate and toluene diisocyanate. Suitable prepolymers of the above types are available from Hampshire Chemical Corp. of Lexington, Mass. as HYPOL PreMA® G-50, HYPOL® 2000, HYPOL® 3000, HYPOL® 4000 and HYPOL® 5000, which formulations generally include copolymers of polyethylene oxide and a minor amount of polypropylene oxide. There are comparable products available from other manufacturers, and comparable prepolymers can be formulated from commercially available raw material.

All things considered, the main chain of the hydrogel polymer is preferably comprised of polyethylene glycol, polypropylene glycol, or a copolymer of polyethylene glycol and polypropylene glycol. It is believed that the non-ionic, hydrophilic properties of polyethylene glycol and polypropylene glycol hydrogels may allow for low levels of non-specific binding of an analyte to the hydrogel and also for good compatibility with immobilized biomolecules so as to maintain native conformation and bioreactivity thereof. Isocyanate-functional hydrogels advantageously absorb large quantities of liquid quickly and in a relatively uniform manner such that the basic overall shape of the gel material is maintained. Furthermore, the moisture absorbed by these materials is retained in the absorbent material even under an applied pressure. Polyurethane-based isocyanate-functional hydrogels of this general type are described in U.S. Pat. No. 3,939,123 (Mathews, et al.), U.S. Pat. No. 4,110,286 (Vandegaer, et al.) and U.S. Pat. No. 4,098,645 (Hartdegan, et al.).

Preferred biochips may be made using an isocyanate-functional hydrogel that is based on a diol or triol of a high molecular weight polyethylene oxide, polypropylene oxide, or a copolymer of polyethylene oxide and polypropylene oxide, capped with water-active diisocyanates, and which may be optionally lightly cross-linked with a suitable cross-linker. It is preferred that the quantity of active isocyanates present in the prepolymer preferably be not greater than about 0.8 meq/g. Generally preferred diisocyanates include aromatic-based diisocyanates, such as toluene diisocyanate or methylene diphenyl-isocyanate, as well as aliphatic diisocyanates, such as isophorone diisocyanate. Preferably, about 0.5% to about 15% of the reactive isocyanates in the polymer are used to provide sites for immobilizing capture agents. The polymerization of the prepolymer for biochip creation, which may be preformulated in a water-miscible organic solvent, may take place by the formation of urea linkages which occur upon the simple addition of water.

The term capture agent is used to refer to material capable of interacting in a specific fashion with one or more target molecules to hybridize with a target or to otherwise interreact and physically sequester a target molecule by a mechanism other than hybridization. Capture agents may include nucleic acids, such as DNA, RNA and PNA which bind via hybridization, and nonhybridization entities in the form of biological material, such as proteins including proteins, receptors, peptides, enzymes, enzyme inhibitors, enzyme substrates, immunoglobulins, e.g. antibodies, antigens, lectins, modified proteins, modified peptides, double-stranded DNA, biogenic amines and complex carbohydrates. Capture agents may also include synthetic molecules, e.g. drugs and synthetic ligands, designed to have specific binding activity of this type. By "modified" proteins or polypeptides is meant those proteins or peptides having one or more amino acids within the molecule altered by the addition of new chemical moieties, by the removal of existing chemical moieties or by some combination of both removal and addition. This alteration may include both natural and synthetic modifications. Natural modifications include, but are not limited to, phosphorylation, sulfation, glycosylation, nucleotide addition, and lipidation. Synthetic modifications include, but are not limited to, chemical linkers to facilitate binding to the hydrogel, and the addition of fluorescent dyes, microstructures, nanostructures, e.g. quantum dots, or other synthetic materials. In addition, modification may include the removal of existing functional moieties, e.g. hydroxyl, sulfhydryl or phenyl groups, or the removal or alteration of native side chains or the polypeptide amide backbone. Examples of complex carbohydrates include, but are not limited to, natural and synthetic linear and branched oligosaccharides, modified polysaccharides, e.g. glycolipids, peptidoglycans, glycosaminoglycans or acetylated species, as well as heterologous oligosaccharides, e.g. N-acetylglucosamine or a sulfated species. Specific examples of naturally-occurring complex carbohydrates include chitin, hyaluronic acid, keratan sulfate, chondroitan sulfate, heparin, cellulose and carbohydrate moieties found on modified protein such as albumin and IgG. Combinations of two or more of capture agents might be immobilized at some locations on the microchip array, which combinations might be added as a mixture of two entities or may be added serially.

Capture agents can be directly or indirectly immobilized in each microspot either prior to, during, or after polymerization of the hydrogel material. Indirect immobilization contemplates the employment of an intermediate agent that is first linked to the hydrogel and possibly a second intermediate agent that is, in turn, linked to it. For example, a first or primary intermediate agent that is encapsulated into the hydrogel matrix might be an antibody directed against calmodulin. Once calmodulin is bound to the antibody, the calmodulin serves as a second intermediate agent when it is utilized, in turn, to sequester calmodulin-binding-proteins, such as the calcium/calmodulin dependent kinase II. This approach to attaching CaM kinase II (as it is commonly referred to) to the hydrogel provides a gentle way of anchoring the protein via a naturally-occurring binding motif, i.e. through the calmodulin protein. The CaM kinase II is now free to probe analyte solutions, for example for the purpose of examining regulatory events on the CaM kinase II (phosphorylation, dephosphorylation), or for searching for possible docking proteins or other intracellular trafficking proteins.

In describing the interaction between an immobilized capture agent and the target as sequestering or nonhybridization binding, it is meant that two or more molecules adhere or bind together in a specific and selective fashion, typically by covalent or non-covalent bonds (e.g., by vander-Waals forces and/or ionic interactions). The specific target can be a simple molecule that may be present in a complex mixture of biological or synthetic materials. The sequestering or binding may be of an extended nature, e.g. covalent modification or antibody-antigen interaction, or it may be transient, e.g. as would occur during a phosphorylation event. Nonhybridization DNA binding entities include, but are not limited to, synthetic and natural double-stranded polymers of deoxyribonucleotides, synthetic and natural poly ribonucleotides, aptamers, and synthetic polynucleotides having one or more modified or non-naturally occurring chemical entity. This alternative use of DNA as a binding/sequestering agent is in contrast to conventional nucleotide hybridization arrays which typically employ single strands of DNA (oligonucleotides or cDNA) to which target DNA hybridizes. Double-stranded DNA might be employed to interact with (as opposed to hybridizing) a suitable biomolecule, such as a DNA binding protein, a transcription factor, e.g. estrogen receptor, or a synthetic drug or molecule, so as to bind or sequester that biomolecule. As an example, general transcription factors, such as TBP or SP1, or gene specific transcription factors, such as nuclear hormone receptors, can be attracted to and sequestered by helical, double stranded DNA. Aptamers are described in U.S. Pat. No. 5,840,867 where they are indicated to function much like monoclonal antibodies.

An initial capture agent may be physically co-polymerized within the gel matrix, e.g. selective antibodies or other selective binding agents, e.g. aptamers; one or more different antibodies may be immobilized in each microspot of an array. Upon subsequent application of a complex mixture of biological materials to such an array, the unique binding attributes of such immobilized antibodies within each microspot would be used to "self-sort" such a complex mixture and create a new array which "self-assembles"; the new array will be complementary to the initial binding entities. For example, an antibody against a specific antigen may be immobilized within each gel microspot during polymerization; thereafter, specific protein or peptide antigens may be provided to bind to each of the cognate antibodies by exposing a mixture of such protein or peptide antigens to such an array. One example of the use of such an intermediate antibody array is to self-sort a complex mixture of proteins from cell extracts without requiring individual isolation of each protein. Such an array thus formed might then be employed to assess what the effect would be on each site of exposure to an added protein kinase or other protein-modifying moiety. This concept might be extended to examine whether such modifying activities would be influenced by drugs or other added chemical compounds.

As a further alternative, other capture agents may be located or anchored within microspots of a biochip array after polymerization through the use of intermediate agents that are initially immobilized. For example, a suitable intermediate, such as Protein A, may be immobilized during polymerization; thereafter, a desired immunoglobin capture agent is bound to the immobilized Protein A by controlled exposure to the immunoglobin in solution.

An initially immobilized capture agent may also be subsequently modified. Such modifications may include (a) biological modifications, e.g. phosphorylation, glycosylation, acetylation, methylation, ubiquitination, lipid modification and ADP-ribosylation, or (b) non-biological modifications, e.g. fluorescent dye modification, biotinylation, alkylation and abnormal residue incorporation, as well as by conjugation with another protein or enzyme to yield an altered final form of the array. Moreover, double-stranded nucleic acid oligonucleotides (or polymers) may be immobilized during polymerization; thereafter, desired proteins may be bound to such nucleic acids by nucleic acid sequence-specific protein interaction to produce a self-assembled protein-nucleic acid complex array.

Furthermore, it may be advantageous to first react the prepolymer with the capture agent in an aprotic solvent. The capture agent becomes effectively immobilized onto the prepolymer, and this procedure may help to subsequently generate a homogeneous solution of the prepolymer in water and may also serve to slow down the generation of carbon dioxide during the polymerization step. If polymerization occurs too quickly in a highly viscous mixture, carbon dioxide gas which is generated is unable to escape and can become trapped within the gel. Such can result in a discrete foam matrix, which may be a problem for continuum of the gel matrix and may interfere with optical transparency. In biochip design, the greater of the optical transparency, the more accurate will be the detection of a signal, such as fluorescence, which is indicative of successful binding to a target.

Ease of diffusion of a prospective target molecule or other secondary binding entity through the porous hydrogel to interact with an intermediate or primary capture agent immobilized within the gel matrix will be determined, in some part, by the percentage of hydrogel prepolymer in the solution that is employed. Although employment of 5% solution of a prepolymer for formulating hydrogel droplets is adequate to create microspots wherein nucleic acid probes will be immobilized, a diffusion of larger molecules, such as proteins, into the polymerized hydrogel formed at 5% level, may be slower than desired. Thus, use of a lower percentage of prepolymer, e.g. 3.5%, is generally preferred to facilitate passage of larger biomolecules into the porous hydrogel. Thus, for many applications, such as those employing antibodies as a visualization tool, the preferred range of polymer may be between about 3% and 5%. Other applications and uses, such as those for examining molecules smaller in size than a typical antibody, e.g. IgG, may respectively employ a higher or lower percentage of polymer in the solution. As explained hereinafter, the pore size should be regulated to prevent the entry of microspheres of a certain size.

Although a hydrogel might be first derivatized with protein capture agents (or intermediates for binding capture agents) and then deposited onto the solid substrate, after initiation but before completion of polymerization thereof, such practice may not be preferred. Generally, delivery of hydrogel prepolymer microdroplets is accomplished by any convenient method as well known in the art; for example, a conventional microspotting machine which deposits gel to form an array of microspots may be used. While such a gel may inherently non-covalently attach to some substrates, a substrate surface is generally derivatized prior to addition of the hydrogel to assure firm attachment of the gel to the substrate. For example where glass is used as the substrate, the glass may be derivatized with amine prior to deposit of the polymerizing hydrogel. The polymerizing hydrogel, already derivatized for example with protein, then binds strongly to the substrate when it is deposited onto the derivatized glass substrate, via reaction of some of its remaining, active isocyanate groups with amines located on the surface of the glass. This provides covalent attachment of the hydrogel microspot to the substrate, and preferably about 5% or less of the active isocyanate groups originally in the prepolymer are used for this function.

In certain embodiments, partial initial blocking of the capture agent may be preferred to maximize its efficient immobilization. For example, the reactivity of the isocyanate prepolymer with certain chemical moieties that a particular capture agent may include, e.g. primary amines, may result in excess crosslinking between the capture agent and the polymer, and such might lead to denaturation of the capture agent or might lower its binding affinity for its target compound. Such might be avoided or limited by protecting at least some of these moieties during polymerization; deprotection after polymerization would then return the functionality and utility of the capture agent within the array, i.e. de-blocking after polymerization would allow the capture agent to assume its native conformation. Such blocking/ de-blocking may be accomplished by either covalent or non-covalent means. For example, when using antibodies as the capture agent, an antigen recognition site susceptible of becoming crosslinked to the polymer may be incubated with an uncrosslinkable peptide (or other epitope mimic) prior to mixing with the prepolymer. Such peptide or epitope mimic would protect the antigen recognition site from conjugation with the reactive isocyanate groups during the polymerization process. Following polymerization, such peptide would be released from the antibody, e.g., by brief exposure to acid, pH 3.0, thus re-exposing the antigen recognition site of the antibody. Similar mechanics can be employed to protect select sulfhydryl moieties or amines on capture agents; these could use well known reversible chemical derivatization to protect these functionalities while polymerization proceeds.

Such hydrogel polymers are suitable for immobilizing a wide variety of other capture agents other than those discussed above, including, but not limited to, materials such as synthetic molecules, drugs, non-peptide receptor ligands, mixed organic/inorganic species, e.g. metal porphyrins, and inorganic materials, e.g. zeolites. For example, such capture agents may be used to sequester compounds from solutions based upon specific interactions between the capture agent and the analyte species.

A non-biological compound, such as a tridentate or tetradentate metal chelating agent, e.g. iminodiacetic acid or nitrilotriacetic acid, having a proper linker of amine-derivatized $C_4$-$C_8$, may also immobilized within the hydrogel as an intermediate capture agent, either prior to or during polymerization. The desired capture agent, e.g. a protein, is preferably synthesized or modified so as to have a multiple histidine-containing sequence, e.g. as a terminus on the tail or head of the protein, and such can then be immobilized to each microspot of the biochip by exposure along with a divalent or trivalent metal ion, such as $Cu^{++}$ or $Fe^{+++}$, so as to allow chelation with such a terminal residue to physically immobilize the protein within the hydrogel by linking to the immobilized chelating agent. By exposing each microspot to a particular capture agent, e.g. a different protein capture agent, a protein chip that is stable for analytical use is formed. One advantage of employing an intermediate agent in creating such a polymer microspot is the greater assurance that potential denaturation of a particularly susceptible protein is avoided so that the conformation and configuration of the ultimate capture agent protein remains unaltered. Also, fabrication may be simplified by the use of the same chelating agent for creating each microspot or cell in a particular protein microarray and then subsequently linking the capture agents thereto.

Advantageously, all reactions involved in this system, namely (1) the derivatization of hydrogel prepolymer either directly with the protein probe or with an intermediate agent, (2) the polymerization of hydrogel and (3) the binding of derivatized hydrogel to the substrate surface, involve the formation of strong urea or urethane (carbamate) bonds. These bonds endow the microspot array with mechanical integrity and significantly increase the half-life of the biochip.

It is generally preferable to load the capture agent into the hydrogel after polymerization of the hydrogel microspot, and occasionally simple diffusion may be an ineffective tool by which to accomplish this. Small molecules that rapidly diffuse into the hydrogel may, in the course of subsequent use, readily diffuse out of the hydrogel, thereby causing the loss of these binding entities. Therefore, in the case of such readily diffusable agents, e.g. small molecules and peptides, it may be preferable to covalently conjugate such agents to the polymeric matrix after diffusion into the matrix. One preferred means to accomplish this utilizes a moiety suitable for performing crosslinking, e.g. photoactivated or chemical crosslinking reagents, contained either within the polymer as part of its composition or linked to the small molecule diffusing into the polymer.

In contrast, larger capture agents, e.g. proteins and large segments of DNA, may not efficiently migrate into the hydrogel matrix by passive diffusion. In order to facilitate the diffusion of larger species into the matrix, an electric field may be applied in such a fashion as to cause the controlled migration of a species having a net charge, e.g. proteins, within a solution having a pH value different from the isoelectric point of the protein; this process is termed "electrophoresis". If the hydrogel microspot is within the migration path of the charged species, the charged species undergoes an additional force supplied by the applied electric field in addition to passive diffusional forces, thereby accelerating its insertion into the hydrogel microspot. An advantage of this electric-field-facilitated diffusion is that these larger capture agents will not readily, passively diffuse out of the hydrogel matrix during subsequent assay steps.

Heretofore, the substrate surface not occupied by the hydrogel microspots may have been treated with agents to reduce subsequent non-specific, non-desired adherence thereto of assay reagents, target molecules or other such materials. Such was considered important in those applications where assay reagents may potentially non-specifically bind to the surface and thus increase the amount of background signal observed from the surface, thereby detracting from the effectiveness of the hydrogel microspots for assay purposes. Treatments for such exposed surface regions included the application of activated polyethylene glycol polymers, bovine serum albumin and other such blocking reagents. The present invention obviates the need for such a step; however, such could still be used if desired.

The hydrogel microspots, following polymerization on the substrate and while still hydrated, are preferably at least about 20 μm thick, more preferably at least about 30 μm thick and most preferably at least about 50 μm to 100 μm thick. Shrinkage in all directions occur as dehydration slowly takes place; however, most of the original volume returns upon rehydration. Microspots formed from hydrogels are often generally elliptical in shape, as opposed to the square gel cells previously used in some systems. Such overall larger size permits a significant quantity of capture agents to be immobilized in the gel microspots, thereby reducing the lower detection limit of a biochip and facilitating its use. By decreasing the viscosity of the polymer solution and with appropriate modifications to dispensing mechanisms heretofore used for microspotting onto a biochip substrate, smaller individual microspots can be produced enabling very high-density biochip arrays. If substrates having wells are employed, the microspots are deposited upon the bottoms of the wells.

Following creation of the 3-D microspotted biochip, to immobilize different capture agents within the pores of the polymerized hydrogel microspots, the microarray is contacted with a solution, usually an aqueous solution containing targets of a size that allows binding with the immobilized capture agents with the porous hydrogel material. The contact between the solution containing the analytes is maintained for a sufficient duration of time and at a desired temperature for the binding to occur; this period may be referred to as an incubation period. Depending upon the assay in question, it is found that many of the reagents, e.g. a secondary antibody in a sandwich assay, may be of the "sticky protein variety" i.e. one which has a tendency to stick or bind to the substrate itself, e.g. glass. Once such occurs, when a detectable signal is thereafter provided, for example, when a TSA (tyramide signal amplification) labeled with Cy3 is introduced, the TSA associates not only with the secondary antibodies that are present in the targets which have been bound by the probes in the porous hydrogel, but it also associates with those secondary antibodies which have stuck to the glass. With such an occurrence, there is the creation of high background noise on the glass when signals from the microarray are measured, as by imaging for fluorescent labels using a laser scanner. A similar situation can occur when the analyte solution contains labeled proteins that are sequestered by the capture agents but which likewise have a tendency to nonspecifically adhere to the glass or other substrate.

It has been found that this propensity to create background noise that would interfere with reading the microarray can be essentially ignored until the assaying procedure has been completed through the step of incubation with the solution containing the dissolved and/or suspended analytes. After incubation and/or labeling and prior to reading, the microarray is subjected to a one-step washing operation which includes an appropriate digester that effectively removes any non-specifically bound targets which are exterior of the individual microspots from the surface of the microarray, or that removes at least the labeled portions of such targets. The digester used is presented in a manner so that the labeled targets which are specifically bound to capture agents within the porous hydrogel microspots remain unaffected.

The digester may be bound as a coating to microspheres or to minute solid particles or the like, of a size sufficiently large to prohibit the entry thereof into the porous hydrogel microspots, as described in more detail hereinafter. The selection of the digester to be employed is dependant upon the composition of materials in the analyte liquid and particularly upon those components having the greatest tendency to non-specifically bind or stick to the substrate surface. For example, when the analytes are proteins, digestive enzymes, i.e. proteases, may be used as digesters; when the analytes are cell lysates, i.e. pieces of cell membrane, the digesters may be lysosomes. The protease may be an endopeptidase, such as papain and pepsin, or may be an exopeptidase, such as a carboxypeptidase.

Proteases, when used, are generally chosen based on two factors: 1) their ability to digest antibodies in the analyte liquid and 2) their optimal working temperature and pH range. Based on this, three proteases are generally preferred: papain and pepsin, which cleave the heavy chains of antibodies and which are not specific to any type of protein, and proteinase K, which is used for general digestion of proteins as it cleaves peptide bonds and catalyzes peptide amide hydrolysis. The working temperature for these proteases ranges from about 25° C. to 37° C., with optimum pH being about 2 to 8; more specifically: papain, RT and pH=6; pepsin, RT and pH=2; and proteinase K, 37° C. and pH=7.5. These temperatures and pH values are quite compatible with the working environment of very many proteins and do not cause them to denature.

The digesters are attached to large molecules or to solid particles; for example, gold particles, organic microspheres, dendrimers or even large protein complexes may be used so long as the size is such to prohibit entry into the interior of the porous hydrogel microspots. It is preferred that the particles be at least 1 micron in size, and preferably the particles are not greater than about 50 microns in size, in order to adequately and efficiently present the digesters to the non-specifically bound materials on the substrates surface. Microspheres made from agarose are commercially available in this size range and may be conveniently used. Such microspheres can be coated with papain or with pepsin or with proteinase K, the three preferred proteases mentioned above. A second follow-up washing might be performed with a different digester if the assay is such that there may be radically different antibodies that might non-specifically adhere to the substrate surface or that might result in the binding of both antibodies and other proteins to the substrate; however, it is expected that only a single one-step washing will usually suffice. As an alternative, microspheres coated with different proteases might be employed as part of the same one-step washing.

The washing is carried out preferably with some agitation over a suitable length of time to allow the protease to contact and digest the proteinaceous matter. Generally the washing will take place over a period of between 1 minute and about 90 minutes, with washing for about 30 minutes often being used.

Following of the completion of the washing, the microarray may be optionally rinsed with washing buffer; however, in many instances such rinsing will not be necessary. The digested proteinaceous matter is carried off with the wash liquid, and the microparticles are likewise removed from the surface of the microarray. Following the completion of washing, and any optional rinsing, the microarrays are labeled with tags that will provide detectable signals if such tags were not already present on the potential targets in the analyte liquid.

Label (or "tag") refers to a sustituent that can be attached to a target or analyte which enables its detection and/or quantitation. Examples include radiolabels, such as $^{32}P$, $^{33}P$, $^{35}S$; colorimetric indicators, such as fluorescent, chemiluminescent or colored compounds; ligands such as biotin; and chemical groups that are distinguishable by mass or other spectroscopic properties. More specific examples or suitable labels include xanthine dyes, rhodamine dyes, naphythylamines, benzoxadiazoles, stilbenes, pyrenes, acridines, Cyanine 3 (Cy3) and Cyanine 5. A label or tag may be introduced as part of an analyte, e.g. as by incorporation into nucleic acid directly as a part of a primer, or may be added by chemical reaction or enzymatic reaction to a protein or other analyte. Such a label may comprise a detectible signal or may instead comprise an intermediate ligand to which a substance that provides a detectable signal will subsequently be hybridized or annealed. Such addition of a substance that will provide a detectible signal may be carried out either before or after such a washing step.

Following washing, and optionally rinsing with a suitable buffer-containing solution, the microarray is subjected to reading. If the detectable signals that are included are of a fluorescent nature, the microarray is subjected to fluorescent imaging using a laser scanner or some comparable device. If a different type of colorimetric label is employed or if a radioactive label or one of some other known category is instead used, an appropriate scanner/detector is instead employed to measure the signal from the microspots.

The following examples include the best mode presently known to the inventors for carrying out the invention; however, it should be understood that these examples are presented for purposes of illustration only and are not considered to be in any way limiting upon the scope of the invention which is of course defined by the claims that appear at the end hereof.

EXAMPLE 1

Protein-DNA Interaction on a Biochip

In this experiment, single-stranded DNA is first linked to a hydrogel microspot followed by hybridization to create double-stranded capture agents which are effective to sequester target proteins.

5' amino-modified, single-stranded bacterial λ repressor binding sequence OR2OR1 (wt) and its mutant (mut) carrying a single base mutation at the binding site are printed on aminosilanated slides at 130 μM in 3.75% HYPOL™ polyurethane prepolymer. To validate this present system of removal, four different types of protein systems are individually bound to the glass surface fibrinogen, cell lysates, IL-5 and NFkB, a matching primary antibody and a secondary antibody for each of the four protein systems. The printed slides are enclosed in individual hybridization chambers and are allowed to hybridize to their corresponding complementary sequences at 1 μM in 3×SSC, 0.1% TritonX-100, 5 mM $MgCl_2$ at 45° C. for 18 hours. The resultant double-stranded DNA are then incubated with 1.5 μg/ml Cy3-labeled bacterial phage lambda repressor λCI in binding buffer (50 mM Tris.HCl (pH 7.6), 100 mM NaCl, 1 mM $CaCl_2$, 0.1 mM EDTA, 0.1 mg/ml BSA, 2.5 μg/ml poly(dA-dT), 0.05% Tween 20, 1 mM DTT) in an aqueous solution wherein there are included types of protein systems will individually bind to the glass surface: fibrinogen, cell lysates, IL-5 and NFkB, and a matching primary antibody and a secondary antibody for each of the four protein systems; incubation is at room temperature for 2 hours. The Cy3-labeled λCI is removed at the end of the incubation, and samples of such slides are respectively washed with liquid containing 1 micron agarose microspheres that are respectively coated with papain, with pepsin and with proteinase K. Washing takes place at about 27° C., and a pH of about 7, for 30 minutes. Each slide is then rinsed briefly with binding buffer and then with DI $H_2O$. Each slide is then TSA-labeled with Cy3 which will attach to the secondary antibody if present; it is then imaged by a GSI laser scanner. On a separate slide, double-stranded DNA is stained with SYBR Gold (Molecular Probe) according to manufacturer's protocol and visualized by a GSI laser scanner for its total DNA content.

Binding of the Cy3 labeled λ repressor to its native operon dsDNA sequence is shown by gain of fluorescent signal in the corresponding microspots. The absence of a strong fluorescence in certain mutant spots indicates that the interaction is sequence-specific. Comparison of the SYBR Gold (a double-stranded DNA stain) stained fluorescence of the printed slides, with the Cy3 fluorescence from λ repressor, confirms that it is the sequence-specific λ repressor-λ operon interaction rather than any non-specific protein linking to unevenly printed DNA that gives rise to the Cy3 signal associated with the wild type OR2OR1 sequence. A hundred-fold difference in signal intensity between linking to the wild type sequence as compared to the mutant sequence confirms the specificity of the reaction to the double-stranded DNA that was immobilized within the hydrogel matrix. The absence of significant signal from the regions of the slide surrounding the microspots shows the effectiveness of the protease-coated microspheres in removing nonspecifically bound proteins without affecting complexes within the microspots.

EXAMPLE 2

Antigen-Biochip

This experiment employs the hydrogel platform as a matrix for anchoring antigens as capture agents. Antibody-antigen interactions are routinely employed in a variety of biological assays, and the ability to anchor either component (antibody or antigen) is a desirable feature.

Using the methodology described in Example 1, a protein antigen, human transferrin (0.2 mg/ml), is directly immobilized at different dilutions in 3.3% hydrogel with 5% trehalose, 2 mg/ml BSA onto an amine-coated glass slide. To test the invention, IL-5 is allowed to bind to the slide by attraction to the glass surface. The slide is incubated for 1 hour with mouse ascites fluid containing anti-human transferrin at varying concentrations in aqueous solution. After incubation, the slide is first washed with liquid containing agarose microspheres coated with papain at 25° C., pH 6, for 30 minutes and is then rinsed three times for 10 mins, each time with PBST. The bound mouse, anti-transferrin antibody is visualized by incubating the slide with Cy3-labeled donkey anti-mouse IgG and with Cy3 labeled antibodies for IL-5, followed by laser scanner imaging. A linear dose response over three orders of magnitude of dilutions, i.e. 0.1 to 0.001, is observed. This dose-response relationship indicates the functionality of the antigen anchored within the hydrogel matrix and the permeability of the hydrogel matrix supporting sequential diffusion of antibodies into the matrix as part of the overall assay methodology. The absence of significant signal from the regions of the slide surrounding the microspots shows the effectiveness of the protease-coated microspheres in removing nonspecifically bound proteins without affecting the complexes within the microspots.

EXAMPLE 3

Antibody-Biochip

In this example, an antibody is anchored within the hydrogel matrix, as opposed to anchoring an antigen.

Anti-human transferrin, anti-BSA and anti-BSA antibodies (0.4~0.8 mg/ml) are immobilized in 3.3% hydrogel in the presence of 5% trehalose, 2 mg/ml bovine IgG and 0.5% glycerol on amino-silanated glass slides, following the methodology of Example 1. The slides are subjected to contact with fibrinogen in aqueous solution to permit nonspecific binding to the glass substrate and are then incubated at room temperature overnight with Cy3-labeled individual antigens at a concentration of 1 mg/ml in PBST containing 1% BSA and with Cy3 labeled Abs for fibrinogen. Bound proteins are visualized by laser scanner imaging after first washing with liquid containing agarose microspheres coated with papain at 25° C., pH 6, for 30 minutes and then rinsing with PBST. The presence of labeled target proteins at the sites of the corresponding antibodies on the microarray indicates the retention of functionality of the antibodies in the hydrogel matrix. The absence of significant signal from the regions of the slide surrounding the microspots shows the effectiveness of the protease-coated microspheres in removing nonspecifically bound proteins without affecting the complexes within the microspots.

EXAMPLE 4

Multiple Layer ELISA Assay

The ability to support more complex binding interactions may also be a desired feature for a hydrogel matrix, and in this example, the hydrogel microspots anchor an antibody as a first binding entity. Subsequent specific localization of its antigen is followed by additional binding events for the purpose of visualization.

NFkB monoclonal capture antibody is directly immobilized in 3.3% hydrogel with 5% trehalose, 2 mg/ml Bovine IgG to create microspots on an amino-silanated glass slide. The slide is incubated with mouse antibody for NFkB for one hour, with proper mixing in aqueous solution and at room temperature. After two 15-minute PBST rinses, the slide is incubated with biotinylated rat monoclonal anti-mouse IgG antibody (BD, Pharmingen) at room temperature for one hour. Free antibody is removed by a PBST wash of 15 minutes. The slide is then washed with liquid containing 1 micron agarose micropheres coated with pepsin at room temp. (RT) and pH of 2 for about 30 minutes, followed by 2 PBST rinses. Horseradish peroxidase-conjugated strepta-vidin is subsequently added to the slide for another hour of incubation at room temperature. Cy3-tyramide substrate from a TSA reagent system is added to the slide to fully cover all printed spots, after an extensive wash of strepta-vidin-HRP following recommended protocol. After washing off unreacted substrate, the slide is analyzed by laser scanner imaging. An eight-fold increase in fluorescent signal indicates the presence of bound antigen by the anchoring antibody within the hydrogel. The absence of significant signal from the regions of the slide surrounding the microspots shows the effectiveness of the protease-coated microspheres in removing nonspecifically bound proteins without affecting the complexes within the microspots.

EXAMPLE 5

Multiple Layers Small Molecule Mediated (CaM/Calcineurin)

The following example demonstrates the use of multiple protein interactions mediated by small molecules.

Mouse anti-bovine brain calineurin monoclonal antibody (0.4 mg/ml, Sigma), sheep anti-bovine calmodulin antibody (0.2 mg/ml, Chemicon) and control bovine IgG (0.4 mg/ml) are respectively and directly immobilized in 3.3% hydrogel with 5% trehalose and 2 mg/ml bovine IgG onto an amine-coated glass slide, as per the methodology of Example 1. The slide is subsequently incubated with 0.1 mg/ml bovine calcineurin in 20 mM HEPES (pH 7.6), 130 mM KCl, 0.1% Triton X-100, 10 µg/ml polyglutamic in aqueous solution acid overnight. Cy3-labeled chicken calmodulin is allowed to bind to the calcineurin-treated slide in the presence of 1 mM $CaCl_2$ or 5 mM EDTA in PBST, 1% BSA at room temperature for one hour. The slide is then washed with liquid containing 1 micron agarose microspheres coated with pepsin, at room temperature (RT) and pH of 2 for about 30 minutes, followed by 2 PBST rinses. The bound calmodulin is visualized by laser scanner imaging at the Cy3 excitation and emission wavelengths. A six-fold increase in signal intensity is shown at the anticalcineurin antibody location in the presence of calcium as compared to in its absence and indicates the ability of the hydrogel matrix to support complex biomolecular interactions involving both proteins and small molecules and further that such is unaffected by such treatment with proteases. The absence of significant signal from the regions of the slide surrounding the microspots shows the effectiveness of the protease-coated microspheres in removing nonspecifically bound proteins without affecting the complexes within the microspots.

EXAMPLE 6

Alpha-2-macroglobulin-trypsin Interaction on a Biochip (Electric Field Based Loading)

Alpha-2-macroglobulin is a large plasma protein (mw 800,000) that circulates in the blood specifically to bind to and neutralize proteases; this is a mechanism which protects the body from excessive protease activity, essentially preventing the body from "digesting" itself. The association between alpha-2-macroglobulin and proteases like trypsin is very strong, and alpha-2-macroglobulin immobilized to aga-rose beads has been used to affinity-purify trypsin and other proteases.

Three sets of hydrogel microdroplets are spotted onto an amine-derivatized glass; no effort is made to block future nonspecific binding of fluorescein-labeled protein. The hydrogel microspots each comprise an isocyanate-functional HYPOL® polyurethane prepolymer, and polymerization is initiated by loading with an aqueous solution, and the polymerization kinetics are controlled by pH and temperature. A first set such of hydrogel microspots is loaded with α-2-macroglobulin using an aqueous solution of 50 μL at a concentration of 5 mg/mL PBS. The high molecular weight of α-2-macroglobulin limits rapid diffusion into the hydrogel microspot, and diffusion rate is increased by using a mild electrical current (2.5-5 mV) delivered by a small electrode system. Once α-2-macroglobulin diffuses inside the hydrogel microspots, its large molecular weight prevents significant subsequent diffusion from the microspots. Ferritin is used to provide a negative control protein, as it is known not to bind to trypsin. Ferritin is similarly diffused into a second set of hydrogel microspots using the same electrode system and mild electrical current under the same conditions. A third set of droplets is not loaded with any protein and serves as an additional negative control.

All three sets of microspots are then exposed to FITC-labeled trypsin for about 15 minutes and rinsed with 1% BSA-PBS, pH 7.4 for about 5 minutes. The slide is then washed with a liquid containing 1 micron agarose microspheres coated with pepsin at RT and pH of 2 for about 30 mintues, followed by 2 PBST rinses. Fluorescence intensities are measured with a CCD camera. The absence of significant signal from the regions of the slide surrounding the microspots shows the effectiveness of the protease-coated microspheres in removing nonspecifically bound proteins without affecting the complexes within the microspots.

The results indicate that FITC-labeled trypsin specifically binds to α-2-macroglobulin, its natural ligand, within the hydrogel microspots, and that there is little detectable binding activity to either the negative control protein ferritin, to the hydrogel itself, or to the glass substrate.

Although the invention has been described with respect to a number of different embodiments which include the best modes presently contemplated by the inventors, it should be understood that changes and modifications as would be obvious to one skilled in this art may be made without departing from the scope of the invention which is set forth in the claims appended hereto. For example, although particular fluorophores, such as FITC and Cy3, were used, other fluorophores or other reporters or detectible signals can alternatively be used. Although there are advantages in the use of biochips having a plurality of microspots carrying different capture agents, in certain situations biochips carrying only one capture agent may be suitable. The disclosures of all patents and publications set forth hereinbefore are incorporated herein by reference.

Particular features of the invention are emphasized in the claims which follow.

What is claimed is:

1. A method for the determination of the presence of one or more targets in a sample being analyzed, which method comprises:
   providing a substrate having an upper surface,
   attaching a plurality of 3-dimensional porous microspots of hydrogel to said surface,
   providing different capture agents within the pores of at least some of said plurality of microspots to create a microarray on said surface,
   contacting said microarray with a solution containing targets of a size that allows binding with said capture agents within said porous hydrogel microspots,
   washing said microarray with a liquid following said contacting which liquid contains minute solid particles that carry containing a digester which particles are of such size that they and said digester do not enter said 3-dimensional microspots whereby said digester removes non-specifically bound targets or at least any labeled portions thereof from said upper surface of said substrate without affecting targets specifically bound to capture agents within said porous hydrogel microspots,
   associating labels with said targets either before or after said washing if said targets do not comprise labels at the time of said binding, and
   measuring said washed microarray to detect signals from labeled targets bound within particular microspots.

2. The method according to claim 1 wherein said targets are proteins.

3. The method according to claim 1 wherein said targets are antibodies.

4. The method according to claim 1 wherein said targets are antigens.

5. The method according to claim 2 wherein said digester is an exopeptidase.

6. The method according to claim 2 wherein said digester is an endopeptidase.

7. The method according to claim 2 wherein said digester is proteinase K.

8. The method according to claim 1 wherein said digester is bound as a coating to said minute solid particles.

9. The method according to claim 1 wherein said digester is bound as a coating to said particles, wherein said particles are dendrimers of such size that prohibits entry into said porous hydrogel.

10. The method according to claim 1 wherein said digester is bound as a coating to said particles, wherein said particles are a protein complex greater than 1 micron in size.

11. The method according to claim 1 wherein said upper surface is a solid surface.

12. The method according to claim 1 wherein said capture agents are proteins.

13. The method according to claim 1 wherein said capture agents are antibodies.

14. The method according to claim 8 wherein said minute solid particles are microspheres.

15. The method according to claim 1 wherein said different capture agents are provided within the pores of said microspots by initially immobilizing binding entities within said hydrogel and then diffusing said capture agents in an aqueous solution into said porous hydrogel microspots so as to attach said capture agents to said binding entities.

16. The method according to claim 15 wherein said hydrogel is an isocyanate-functional hydrogel and said binding entities are covalently bound to the isocyanate moieties.

17. The method according to claim 15 wherein said digester is proteinase K.

18. A method for the determination of the presence of one or more targets in a sample being analyzed, which method comprises:
   providing a microarray having a plurality of 3-dimensional porous hydrogel microspots on an upper surface of a substrate,
   providing different capture agents within the pores of at least some of said plurality of microspots,
   incubating said microarray with a solution containing targets of a size that they can bind with said capture agents within said porous hydrogel microspots, associating labels with said targets that do bind to said capture agents in said microspots if said targets do not comprise labels at the time of said binding, washing said upper surface of said microarray with a liquid following said incubating, which liquid contains a digester that is present on the outer surface of minute solid particles that are of such size that they and said digester do not enter said 3-dimensional microspots so that said digester removes non-specifically bound targets or at least any labeled portions thereof from said upper surface of said substrate without affecting said targets specifically bound to capture agents within said porous hydrogel microspots, and measuring said washed microarray to detect signals from said labeled targets bound within particular hydrogel microspots.

19. The method according to claim 18 wherein said targets are antibodies, antigens or other proteins.

20. The method according to claim 19 wherein said digester is an endopeptidase.

21. The method according to claim 18 wherein said minute solid particles are microspheres of at least 1 micron in size and said digester is proteinase K.

22. The method according to claim 18 wherein said different capture agents are provided within the pores of said microspots by initially immobilizing binding entities within said hydrogel and then diffusing said capture agents in an aqueous solution into said porous hydrogel microspots so as to attach said capture agents to said binding entities.

23. The method according to claim 22 wherein said hydrogel is an isocyanate-functional hydrogel and said binding entities are covalently bound to the isocyanate moieties and wherein said labels provide fluorescent signals.

24. A method for the determination of the presence of one or more targets in a sample being analyzed, which method comprises:

providing a microarray having a plurality of 3-dimensional porous hydrogel microspots at least about 20 μm thick on an upper surface of a substrate, providing different capture agents within the pores of at least some of said plurality of microspots, incubating said microarray with a solution containing labeled targets of a size that they can bind with said capture agents within said porous hydrogel microspots, washing said upper surface of said microarray with a liquid following said incubating, which liquid contains a digester that is present on the outer surface of minute solid particles at least 1 micron in size that do not enter said 3-dimensional microspots so that said digester removes non-specifically bound targets or at least any labeled portions thereof from said upper surface of said substrate without affecting said labeled targets specifically bound to capture agents within said porous hydrogel microspots, and measuring said washed microarray to detect signals from labeled targets bound within particular hydrogel microspots.

* * * * *